United States Patent [19]
Stark et al.

[11] Patent Number: 5,823,975
[45] Date of Patent: Oct. 20, 1998

[54] LOCAL MONITORING SYSTEM FOR AN INSTRUMENTED ORTHOPEDIC RESTRAINING DEVICE AND METHOD THEREFOR

[76] Inventors: John G. Stark, 19390 Walden Trail, Deephaven, Minn. 55391; Shawn B. Dempster, 45 Island Rd., North Oaks, Minn. 55127

[21] Appl. No.: 804,950

[22] Filed: Feb. 24, 1997

Related U.S. Application Data

[63] Continuation of Ser. No. 388,879, Feb. 15, 1995, abandoned, Continuation-in-part of Ser. No. 298,591, Aug. 31, 1994, Pat. No. 5,484,389, which is a continuation of Ser. No. 733,207, Jul. 19, 1991, Pat. No. 5,368,546, which is a continuation of Ser. No. 483,139, Feb. 21, 1990, Pat. No. 5,052,375.

[51] Int. Cl.[6] ............................................. A61B 5/00
[52] U.S. Cl. ............................................................ 600/595
[58] Field of Search ........................... 128/774, 779, 128/782, 869, 870, 876, 882; 601/33, 34; 600/587, 592, 595; 340/573, 665, 678, 815.4

[56] References Cited

U.S. PATENT DOCUMENTS

| | | | |
|---|---|---|---|
| 5,000,169 | 3/1991 | Swicegood et al. | 128/882 |
| 5,227,874 | 7/1993 | Von Kohern | 358/84 |
| 5,435,321 | 7/1995 | McMillen et al. | 128/782 |
| 5,474,083 | 12/1995 | Church et al. | 128/782 |
| 5,474,088 | 12/1995 | Zaharkin et al. | 128/782 |

*Primary Examiner*—Max Hindenburg
*Attorney, Agent, or Firm*—Robert A. Elwell

[57] ABSTRACT

A system and method for locally monitoring an orthopedic restraining device is provided. The restraining device restrains movement of a first flexibly connected body portion relative to a second body portion of an individual wearing the restraining device. Communication is accomplished by receiving a message signal from a restraining device controller operatively coupled to the personal orthopedic restraining device. The message signal is encoded into a display compatible signal. Subsequently, the display compatible signal is prepared for subsequent transmission by modulating the display compatible signal. Finally, the modulated display compatible signal is transmitted over a communication channel to the local monitoring unit such that the individual wearing the restraining device can receive messages from the restraining device controller. In addition, the operations of the local monitoring unit which displays a message from the restraining device controller based on contents of the display compatible signal are described.

23 Claims, 10 Drawing Sheets

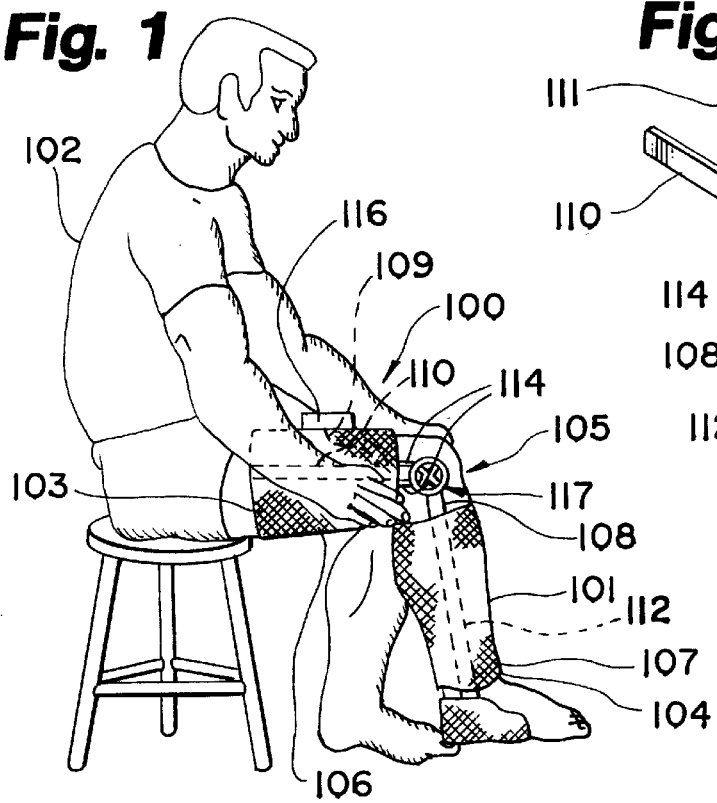
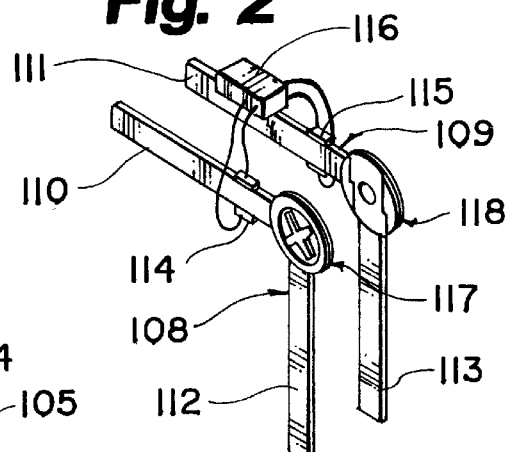
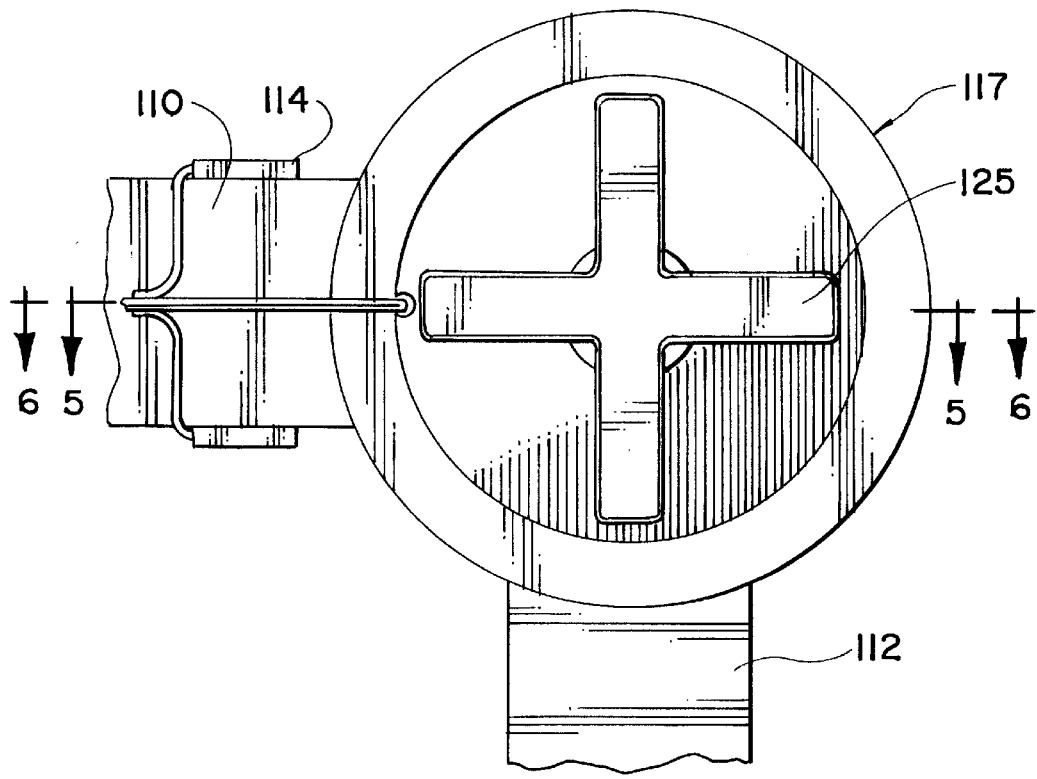

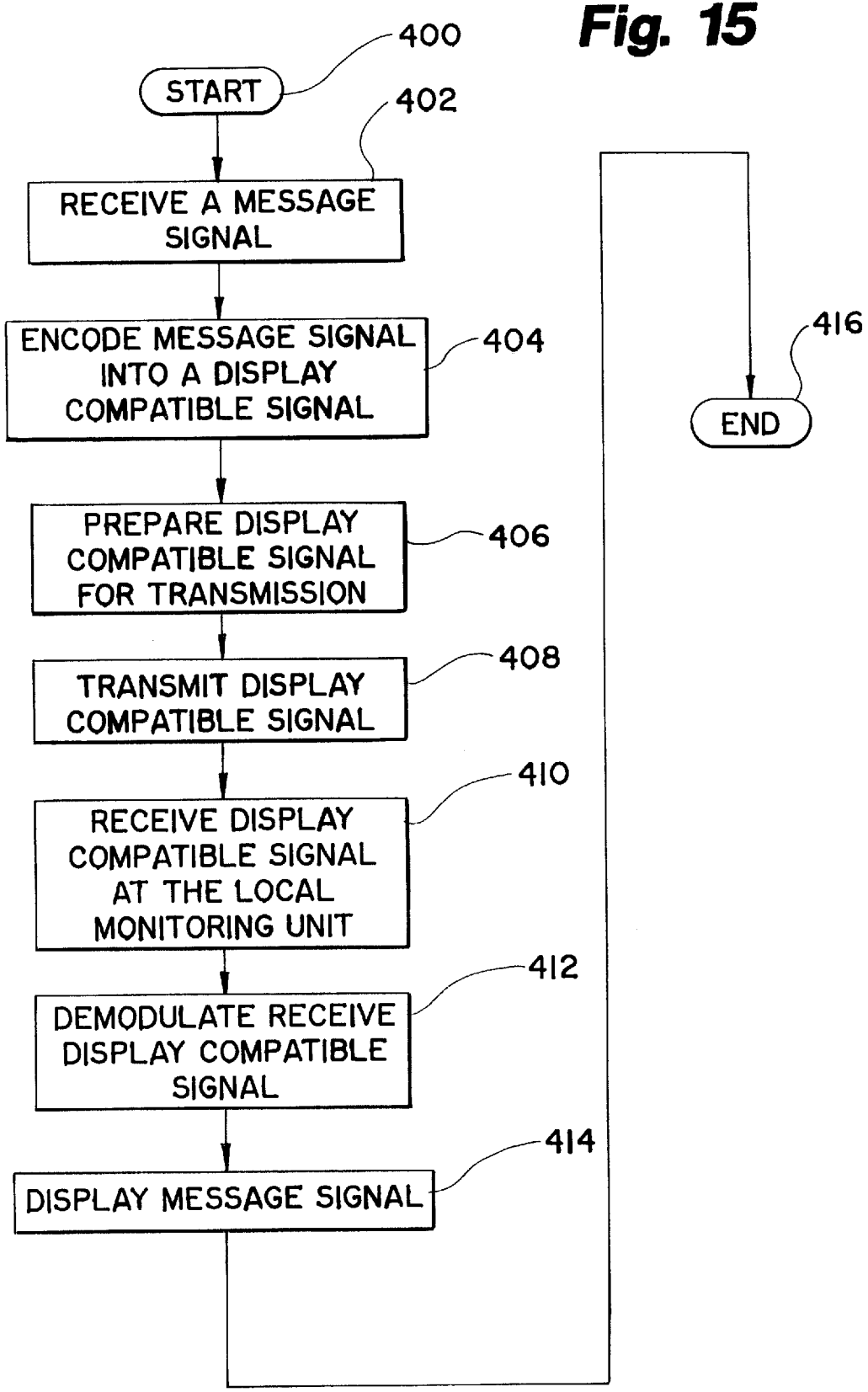

LOCAL MONITORING SYSTEM FOR AN INSTRUMENTED ORTHOPEDIC RESTRAINING DEVICE AND METHOD THEREFOR

This is a continuation Ser. No. 08/388,879 filed Feb. 15, 1995, now abandoned; which was a continuation-in-part of Ser. No. 08/298,591 filed Aug. 31, 1994, entitled "Instrumented Orthopedic Restraining Device and Method of Use" now U.S. Pat. No. 5,484,389; which is a continuation of Ser. No. 07/733,207 filed Jul. 19, 1991 entitled "Instrumented Orthopedic Restraining Device and Method of Use" now U.S. Pat. No. 5,368,546; which is a continuation of Ser. No. 07/483,139 filed Feb. 21, 1990, entitled "Instrumented Orthopedic Restraining Device and Method of Use"now U.S. Pat. No. 5,052,375.

RELATED INVENTIONS

The present invention also is related to U.S. patent application Ser. No. 08/xxx,xxx, filed concurrently herewith on February xx, 1995, which is entitled "Communication System For An Instrumented Orthopedic Restraining Device And Method Therefor"by Stark et al., and which is assigned to the assignee of the present invention.

FIELD OF THE INVENTION

The present invention relates generally to ambulatory orthopedic restraining devices such as casts, braces and the like. More particularly, the present invention relates to a local monitoring system for monitoring operations of an orthopedic restraining device.

BACKGROUND OF THE INVENTION

It is known that both muscles and bones should be exercised to maintain strength. It is also known that healing fractures, exposed to permissible weight bearing stress, often heal more predictably and more rapidly than fractures which are not stressed at all. This is probably also true for connective tissues, such as ligaments and articular cartilage.

When an individual sustains a physical injury which involves damage to bones, muscle tissue, connective tissue or the like, the physician treating the individual will make a determination as to whether exercise will be allowed. The physician will allow exercise if the physician can obtain assurances that the exercise will be performed in a controlled manner within specific parameters wherein the injured bone and/or tissue will remain stable. Unfortunately, however, the physician is generally unable to obtain adequate information or assurances about the manner in which a particular patient will conduct prescribed exercise. Furthermore, because the physician is also unable to obtain adequate feedback after the patient performs any specific prescribed exercise, the physician generally does not feel he or she has sufficient access to information about the exercise to permit or recommend anything but the most basic exercise. Without some way to obtain information about exercise events, the physician cannot maintain sufficient control of the exercise. The physician does not know how much stress the patient can or will exert voluntarily, and does not know how well the patient will adhere to a schedule of repetitive exercise events.

Since the physician is not able to obtain adequate feedback regarding the patient's exercise, the most prudent course of action for the physician is to limit the amount of exercise which the patient is allowed to perform by immobilizing the portions of the body proximate the injury. This is often accomplished by using a cast which is the simplest and crudest method of protecting an injury. The cast allows virtually no movement at all and is widely used to insure against reinjuries. Unfortunately, this method of protecting the injury often does not provide adequate means for exercising the body portions proximate the injury. For instance, a cast is often not strong enough, without additional reinforcement, to permit appropriate isometric exercising. Furthermore, casts are not equipped to provide feedback to the physician or the patient with respect to any exercising.

Accordingly, a need exists for a personal orthopedic restraining device which will permit and encourage a range of exercise during rehabilitation and provide sufficient feedback to the prescribing physician to allow the physician to evaluate the patient's progress in regard to the exercise the physician has prescribed. A need also exists for a personal retraining device which is equipped to give the patient immediate feedback respecting exercise events. Although it has been known that exercise is helpful in rehabilitating patients and others having orthopedic disabilities, inadequacies, or the like, adequate devices for methods of retraining respective body parts and monitoring the exercise thereof have not been provided which adequately address this problem. This monitoring can be enhanced by utilizing a local monitoring system which provides feedback to the individual wearing the orthopedic restraining device. An integral part of this local monitoring system is a communication system between the restraining device and a local monitoring unit.

Communication systems take many forms. In general, the purpose of a communication system is to transmit information-bearing signals from a source, located at one point, to a user destination, located at another point some distance away. A communication system generally consists of three basic components: transmitter, channel, and receiver. The transmitter has the function of processing the message signal into a form suitable for transmission over the channel. This processing of the message signal is referred to as modulation. The function of the channel is to provide a physical connection between the transmitter output and the receiver input. The function of the receiver is to process the received signal so as to produce an estimate of the original message signal. This processing of the received signal is referred to as demodulation.

Modulation can be accomplished in many different ways, including amplitude modulation (AM) in which a bandwidth of only twice that of the information itself is used. Low deviation frequency modulation (FM) as well as single sideband AM, also permit information to be transmitted in a bandwidth comparable to the bandwidth of the information itself.

It will be appreciated by those skilled in the art that several other forms of modulation exist; however, they are more complex and costly to implement. As such they are not suitable for the low cost, high volume application described herein in which each instrumented personal orthopedic restraining device would be provided with a local monitoring system. In addition, it is desirable to follow current federal communications commission (FCC) rules in such manner that no license is required to operate such local monitoring system if particular frequencies are used.

The present invention provides a solution to these and other problems, and offers other advantages over the prior art.

SUMMARY OF THE INVENTION

The present invention provides a local monitoring system for an instrumented orthopedic restraining device (e.g., a brace). This local monitoring system provides a message signal to a local monitoring unit such that a patient wearing a brace can receive messages from a restraining device controller.

In accordance with a first aspect of the invention, a communication unit is provided. The communication unit includes a data input which receives a message signal from a restraining device controller (microprocessor) operatively coupled to a personal orthopedic restraining device. The restraining device restraining movement of a first flexibly connected body portion relative to a second flexibly connected body portion of an individual wearing the restraining device. An encoder is operatively coupled to the data input to encode the message signal into a display compatible signal. A modulator is operatively coupled to the encoder to prepare the display compatible signal for subsequent transmission by modulating the display compatible signal. Also, a transmitter is operatively coupled to the modulator to transmit the modulated display compatible signal over a communication channel to a local display device such that the individual wearing the restraining device can receive messages from the restraining device controller.

The message signal preferably is one or more of the following, including: a message to the individual wearing the personal orthopedic restraining device from a central site monitoring station, a message to initiate an exercise regimen, and/or a representation of a variance between an exercise goal and a current exercise regimen. In addition, the message signal preferably consists of display driver commands which can be directly used by a display device to drive a display mechanism.

It will be appreciated by those skilled in the art that the modulator may modulate the display compatible signal according to one of several communication access types. However, in an effort to simplify the monitoring system either amplitude modulation or frequency modulation preferably are used. Also, the communication channel may be one of several short range types, including: an electronic data bus, radio communication link, infrared, wireline or optical fiber link. The type of communication channel can also be described which reference to a particular channel known in the art. Some of the possible currently existing channels that may be used include a serial port wireline, a parallel port wireline, an infra-red link, and/or a radio link.

In accordance with a second aspect of the invention, a local monitoring unit is provided. The local monitoring unit includes a receiver which receives a modulated display compatible signal over a communication channel from a personal orthopedic restraining device controller. A demodulator is operatively coupled to the receiver to demodulate the received modulated display compatible signal into a display compatible signal. A video display is operatively coupled to the demodulator to display a message from the restraining device controller based on contents of the display compatible signal.

As previously noted with respect to the communication unit attached to the restraining device, the communication channel can be one of several types and kinds. In addition, the message from the restraining device controller preferably consists of a message to the individual wearing the personal orthopedic restraining device from a central site monitoring station, a message to initiate an exercise regimen, and/or a representation of a variance between an exercise goal and a current exercise regimen.

The video display preferably includes a video source input operatively coupled to the demodulator such that the display compatible signal directly drives a display mechanism within the video display. This display mechanism may be one of several kinds, including: a liquid crystal display, a light emitting diode array, and/or a cathode ray tube video monitor.

The communications unit and the local monitering unit can be used in device-implemented methods to communicate an message signal between a personal orthopedic restraining device and a local monitoring unit. One of these communication methods includes receiving a message signal from a restraining device controller operatively coupled to the personal orthopedic restraining device. Subsequently, the message signal is encoded into a display compatible signal. The display compatible signal is prepared for subsequent transmission by modulating the display compatible signal. Finally, the modulated display compatible signal is transmitted over a communication channel to the local monitoring unit such that the individual wearing the restraining device can receive messages from the restraining device controller.

Another of the communication methods includes receiving a modulated display compatible signal over a communication channel from a personal orthopedic restraining device controller. Subsequently, the received modulated display compatible signal is demodulated into a display compatible signal. Finally, a message from the restraining device controller based on contents of the display compatible signal is displayed.

This message signal from the personal orthopedic restraining device controller preferably is either a message to the individual wearing the personal orthopedic restraining device from a central site monitoring station, a message to initiate an exercise regimen, or a representation of a variance between an exercise goal and a current exercise regimen.

These and various other features as well as advantages which characterize the present invention will be apparent upon reading of the following detailed description and review of the associated drawings.

BRIEF DESCRIPTION OF THE DRAWINGS

FIG. 1 is a side view of an orthopedic straining device in accordance with the present invention.

FIG. 2 is a schematic illustration of the orthopedic restraining device show in FIG. 1 showing elongated restraining bars located on either side of the device.

FIG. 3 is an enlarged side view of an incrementally adjustable hinge shown in FIG. 1.

FIG. 15 is a flowchart of the preferred embodiment operations of the local monitoring system as shown in FIG. 13 in accordance with the present invention.

DETAILED DESCRIPTION OF THE PREFERRED EMBODIMENT

Figure 4:
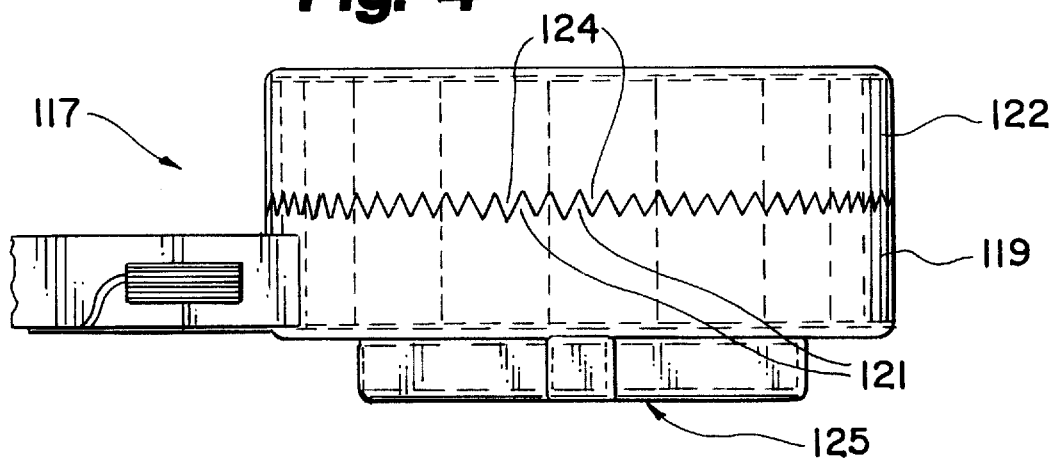
FIG. 4 is a top view of the adjustable hinge shown in FIG. 1 when its respective engaging members are engaged.

Referring now to the drawings, and to FIGS. 1–2 in particular, a personal orthopedic restraining device 100 in accordance with the present invention is illustrated when engaged with upper and lower leg portions of a right leg 101 of an individual 102. It will be appreciated by those skilled in the art that the techniques described herein with respect to a knee brace can readily be applied to other braces attached to joints such as the hip, elbow, shoulder, back, ankle, wrist and neck without departing from the scope and spirit of the present invention.

The restraining device 100 includes a housing 105. The housing includes first and second distal end portions 106 and 107 which are configured to receive upper and lower leg portions 103 and 104 of the individual's right leg 101 which are flexibly connected at the knee. The housing 105 further includes a pair of elongated restraining bars 108 and 109 disposed on opposite sides of the individuals right leg 101. Each of the elongated restraining bars 108 and 109 have first and second distal end sections 110 and 111, and 112 and 113, respectively. Each of the distal end sections is fixedly secured to the respective end portion of the housing proximate thereto. Attached to opposite edges of each of the elongated restraining bars 108 and 109 are separate strain gauges 114 and 115 respectively. In preferred embodiments the strain gauges 114 and 115 are foil type strain gauges, each consisting of two strain gauges such that each elongated bar member 108 and 109 are equipped with four strain gauges which are interconnected in a wheatstone bridge circuit arrangement to provide superior sensing capabilities. The strain gauges are capable of sensing stress on the elongated restraining bars and provide an output which is indicative of a quantitative stress level. The strain gauges 114, 115 are electrically interconnected with a programmed microprocessor control unit 116 which includes a mechanism for indicating a quantitative stress value based upon an output from the strain gauges 114, 115 which sense stress on the respective elongated bar members 108 and 109 to which the individual strain gauges are attached.

An isometric restraining device 100 in accordance with the present invention includes a restraining mechanism 105 including an elongated restraining bar 108, two strain gauges 114 attached to the restraining bar 108, and a control unit 116, including a stress indicating mechanism, interconnected to the strain gauges 114. The restraining device 100 also includes a second elongated restraining bar 109 proximate the inside of the subject's leg in FIG. 1. The other restraining bar 109 also equipped with two strain gauges 115 which are attached to the bar and electrically interconnected to the control unit 116 in a similar manner to that shown in FIG. 1. Both restraining bars 108 and 109 are shown in FIG. 2.

In addition, each of the elongated restraining bars 108 and 109 include an incrementally adjustable hinge 117 or 118 interconnecting the respective distal end sections 110 and 112; or 111 and 113. The first and second distal end portions 106 and 107 of the housing 105 are interconnected by the elongated restraining bars 108 and 109 which are fixedly secured thereto. The respective first distal end sections 110 and 111 are fixedly secured to the first distal end portion 106 and the second distal end sections 112 and 113 are fixedly secured to the second distal end portion 107 so that these elements of the alternate restraining device 100 move as though they were separate portions of an integral unit.

It will be appreciated that the present invention may be made with a single strain gauge attached to a single elongated bar. However, it is preferable to include an elongated bar on either side of a point of flexion such as a knee, an elbow or the like. Similarly, it is preferable to include at least two strain gauges 114, 115 on each of the elongated bars 108, 109 and, preferably, four strain gauges in an unbalanced wheatstone bridge circuit arrangement or configuration.

Figure 5:
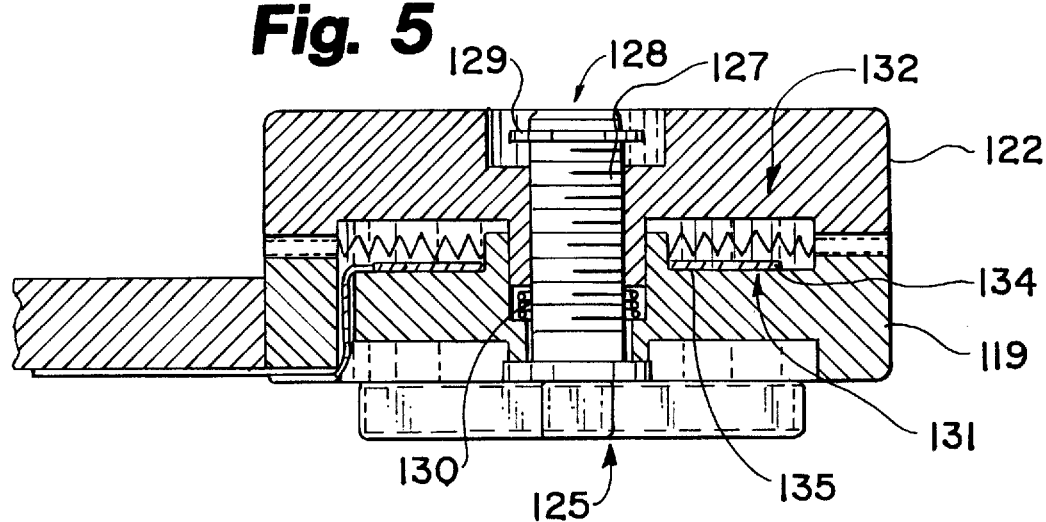
FIG. 5 is a sectional view of the adjustable hinge from the line 5—5 of FIG. 3 when the respective engaging members are engaged.
Figure 6:
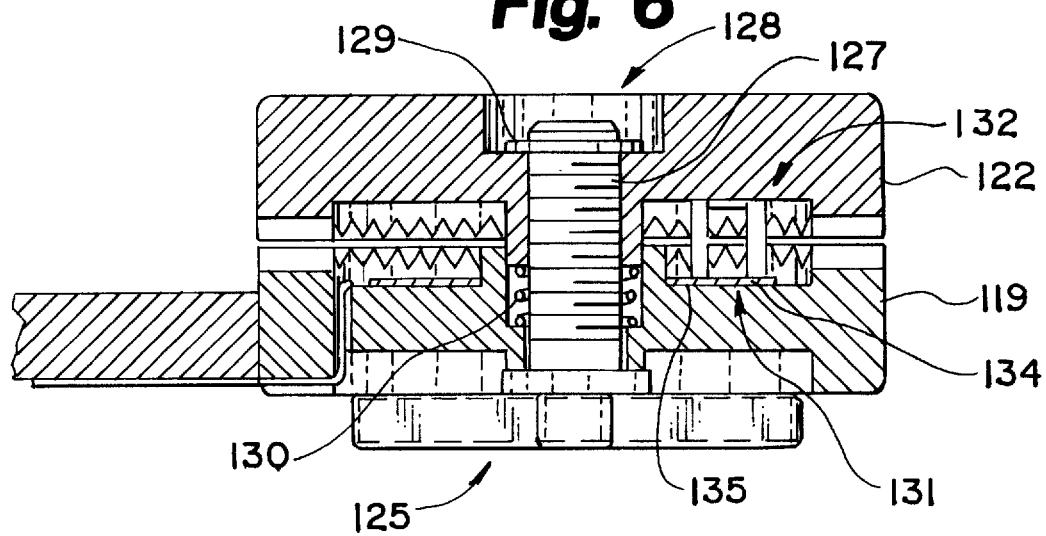
FIG. 6 is a sectional view of the adjustable hinge from the line 6—6 of FIG. 3 when the respective engaging members are disengaged.

Referring now also to FIGS. 3–8, the adjustable hinge apparatus 117 includes a first engaging member 119 which can be engaged with a second engaging member 122. The first engaging member 119 is interconnected with the first distal end section 110 of the elongated restraining bar 108 and the second engaging member 122 is interconnected with the second distal end section 112 of the elongated restraining bar 108. Each of the respective engaging members include engaging teeth, 121 and 124 respectively, which engage one another in a reciprocal relationship when the respective engaging members 119 and 122 are tightened or screwed together as shown in FIGS. 4 and 5. When the respective engaging members 119 and 122 are not tightened together, as shown in FIG. 6, they are free to turn or pivot with respect to one another on a bolt portion 127 of a securing member 125 which is retained within a bolt receiving opening 128 in the second engaging member 122. The bolt receiving opening 128 is located in the circumferential center of the second engaging member 122 so that the bolt portion 128 of the securing member 125 provides an axial pivot point for the respective engaging members 119 and 122, with respect to one another, when they are not secured together.

The bolt portion 127 of the securing member 125 is retained in the bolt receiving opening 128 be a retaining clip 129 which is attached to the bolt portion 127 such that the bolt portion 127 cannot be removed from the bolt receiving opening 128. This prevents the securing member 125 from becoming entirely disengaged from the second engaging member 122 when the securing member 125 is unscrewed to free the engaging teeth 121 of the first engaging member 119 from the engaging teeth 124 of the second engaging member 122. When the securing member 125 is unscrewed as far as the retaining clip 129 will allow the bolt portion 127 will bias the first engaging member 119 away from the second engaging member 122 so that the respective engaging teeth 121 and 124 are disengaged and the respective engaging members 119 and 122 can turn or pivot about the bolt portion 127 of the securing member 125.

The bolt receiving opening 128 of the second engaging member 122 includes a reciprocating screw hole which receives and reciprocates the right-handed screw turns on the bolt portion 127 of the securing member 125. The bolt receiving opening 128 also includes a recess. When the securing member 125 is turned clockwise, the right-handed screw turns of the bolt portion 127 are drawn into the second engaging member 122 by the reciprocating turns of the reciprocating screw hole, and the respective engaging teeth 121 and 124 are gradually drawn closer together. When the securing member 125 is turned as far as it can go in this direction, the coil spring 130 will be tightened together as shown in FIG. 5 and the respective engaging teeth 121 and 124 will be tightened together and engaged such that the respective engaging members 119 and 122 can no longer turn or pivot with respect to one another.

When the engaging members 119 and 122 are tightened together in this manner, as shown in FIGS. 4 and 5, an angle between the respective distal end sections 110 and 112 of the elongated restraining bar 108 will be fixed and the device 100 can then be used to restrain an individual wearing or engaged in the device 100 conducting isometric or other exercises sat a series of different degree of flexion generally corresponding to this angle. This device 100 can also be used to restrain an individual conducting isometric exercises at a series of different degrees of flexion. This can be accomplished by conducting isometric exercises at one degree of flexion when the respective distal end sections 110 and 112 are set at one particular angle with respect to one another, and subsequently at a second, third, fourth and/or fifth degree of flexion when the respective distal end sections 110 and 112 are reset at different angles. It will be understood that this will mean resetting the angle between the respective end sections of each of the restraining bars 108 and 109 in a preferred device 100 which has two restraining bars. This is done by loosening the respective securing members 125 and 126 (not shown) on each side of the device 100, allowing the individual to adjust the flexion of the joint manually, and resecuring the respective engaging members 119 and 122 of the respective adjustable hinge apparatus 117 and 118, such that the respective engaging teeth 121 and 124 of both of the adjustable hinges 117 and 118 are fully engaged as shown in FIGS. 4 and 5. When the engaging teeth are fully engaged, and the respective engaging members can no longer pivot with respect to one another, the angle between the respective distal end sections will be fixed and the subsequent isometric exercising can begin.

Preferred embodiments of the present invention also include a control unit 116. The control unit is interconnected with the respective strain gauges and the incrementally adjustable hinges in order that the control unit 116 can receive electrical outputs therefrom. The incrementally adjustable hinge 117 preferably includes a potentiometer-like mechanism which is used as a position sensing device 131 for determining the angle of the respective distal end sections of the respective elongated restraining bar 108, 109 in respect to one another. It will be appreciated that because the angle between respective end sections of respective restraining bars will generally be roughly equivalent, it is not required to have more than one potentiometer mechanism in any device 100. However, because the elongated restraining bars 108 and 109 of the present device 100 are identical mirror images of one another, each includes the adjustable hinge apparatus 117 and 118, respectively, including a potentiometer mechanism 131 which is interconnected with the control unit 116. Each potentiometer mechanism has the same elements. Further embodiments of the hinge mechanism may include modification to better approximate the specific anatomic motion of the respective joint partially immobilized or protected by the specific device.

Figure 7:
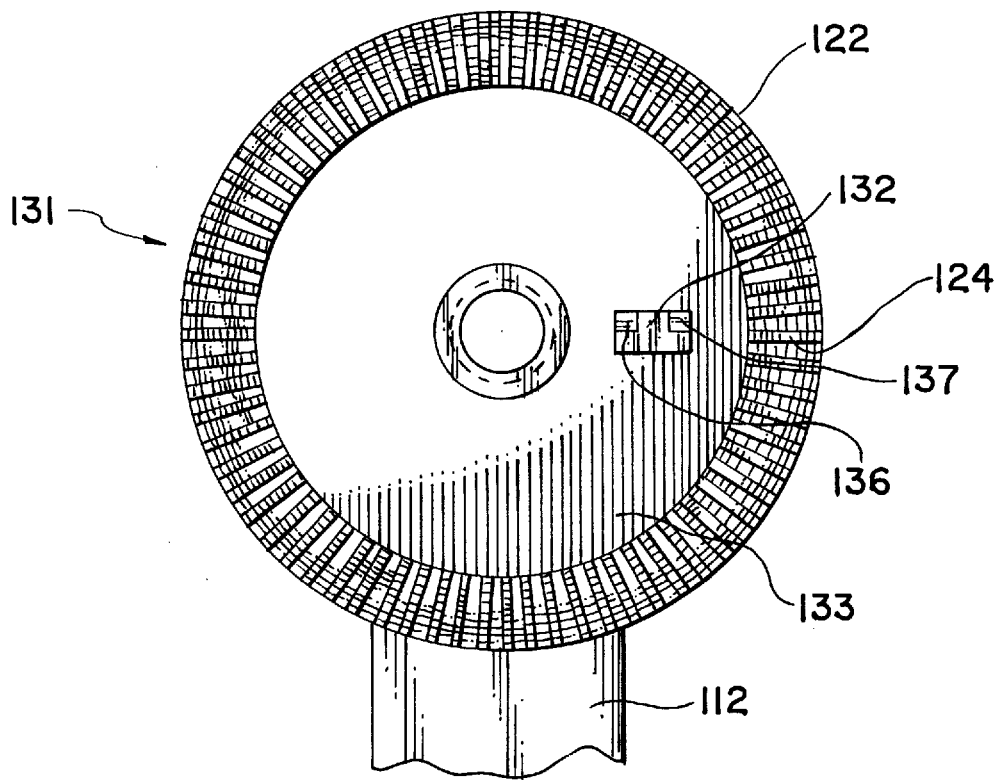
FIG. 7 is a side plan view of a fist engaging member of the adjustable hinge shown in FIG. 4.
Figure 8:
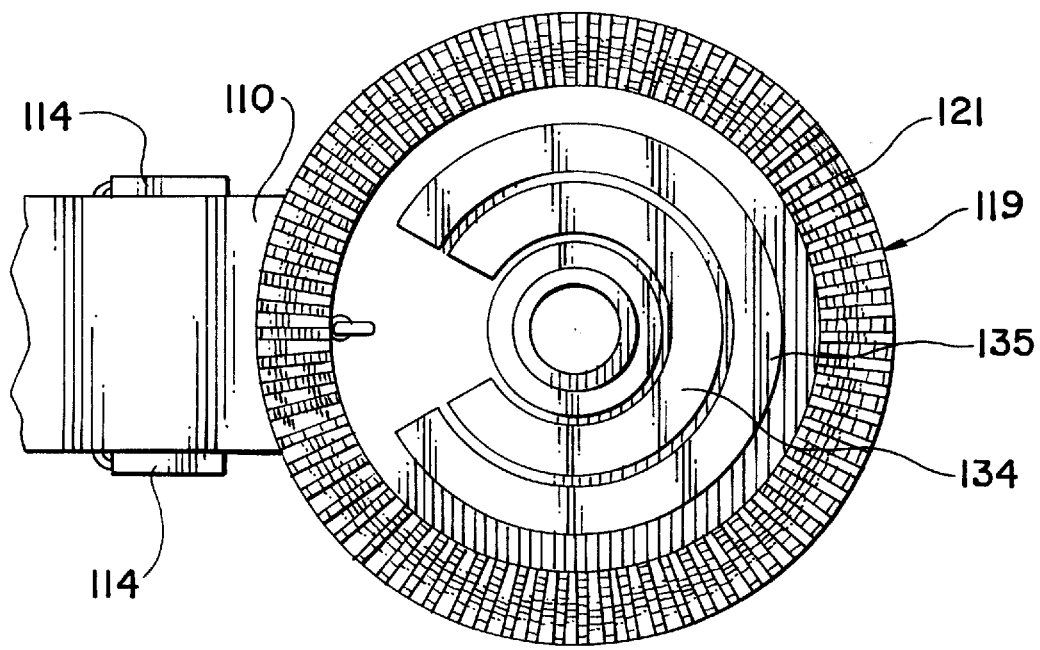
FIG. 8 is a side plan view of a second engaging member of the adjustable hinge show in FIG. 4.

The position sensor's potentiometer mechanism 131 shown in FIGS. 5 and 6 includes a conductive wiper 132 attached or adhered to an inner surface 133 of the second engaging member 122, a resistive element 134 and a conductive element 135 which are interconnected with the control unit 116 in order that outputs from the potentiometer mechanism 131 can be monitored, and preferably, recorded, by the control unit 116 (See FIGS. 7 and 8 also). The wiper 132 has two resilient contact arms 136 and 137 which extend outwardly from the inner surface 133 of the second engaging member 122 to contact the resistive element 134 and the conductive element 135, respectively, so that the position of the wiper 132 with respect to the resistive element 134 can be sensed by the control unit 116 reading the electrical output from the potentiometer mechanism 131. In embodiments where there are two hinges only one of the potentiometer mechanisms, if there are two, needs to be interconnected with the control unit 116, although both can be connected.

Figure 9:
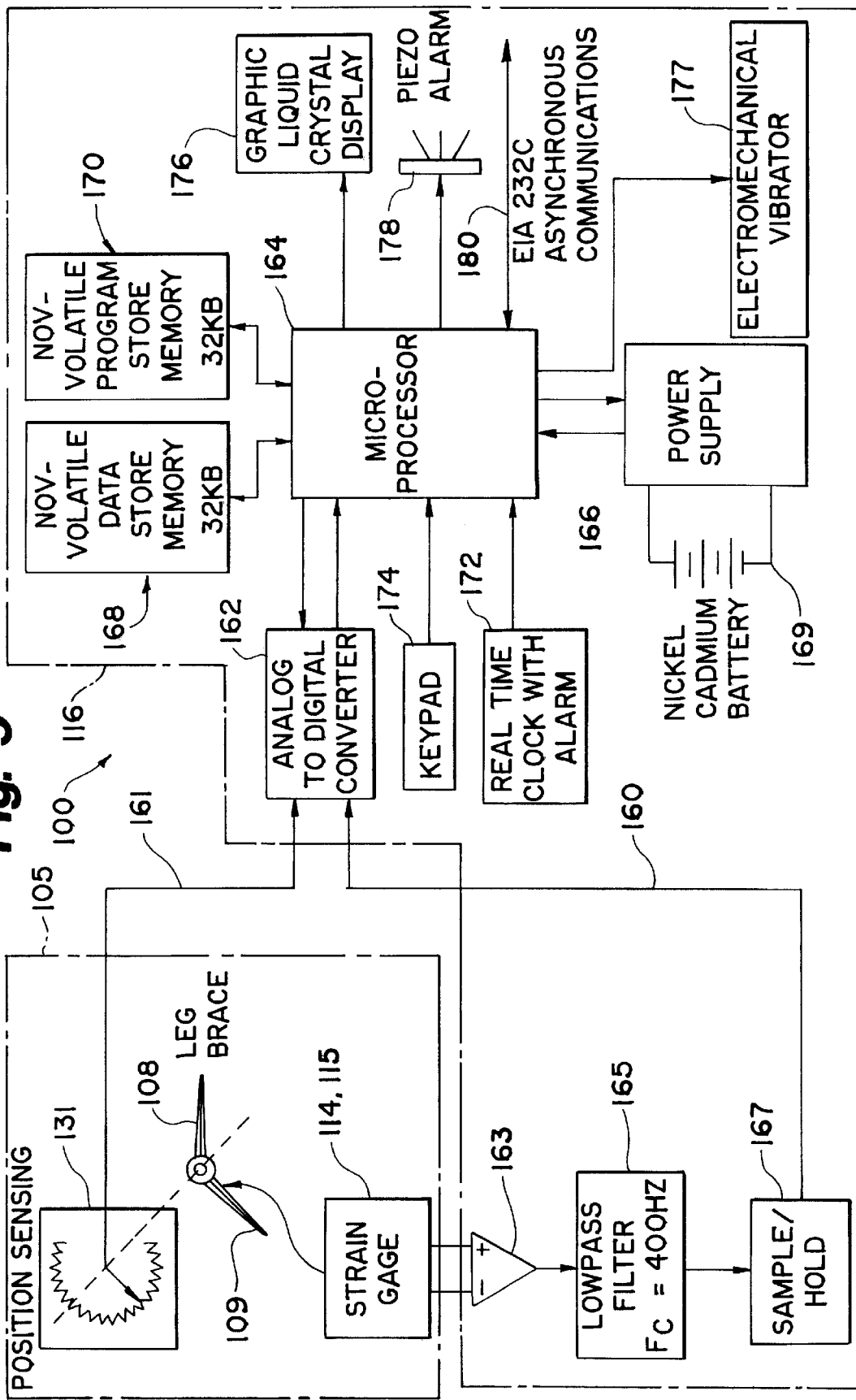
FIG. 9 is a functional block diagram of the orthopedic restraining device shown in FIGS. 1–8.

Illustrated in FIG. 9 is a functional block diagram of the control unit 116 of the orthopedic restraining device 100 shown in FIGS. 1–8. The control unit 116 preferably controls certain aspects of the operation of the orthopedic restraining device 100. The housing 105 of the orthopedic restraining device is schematically represented by the broken line 105 and the control unit 116 is schematically represented by the broken line 116. The various components of the control unit 116 are illustrated as being suitably electrically connected. The control unit 116 receives analog input signals from the position sensor 131 configured and arranged for sensing the relative angular position of the first and second distal end sections of the orthopedic restraining device 100, and the control unit 116 also receives signals from a stress sensing mechanism, in the embodiment shown the strain gauges 114, 115, for sensing stress on the orthopedic restraining device 100. The signals received from the position sensor 131 are representative of the sensed relative angular position and the signals received from the strain gauges 114, 115 are representative of the sensed stress. In the embodiment shown, control unit 116 shown thus receives two general types of input signals: one representative of the angular position of the orthopedic restraining device 100 and a second representative of the strain on the orthopedic restraining device. The position sensor 131 is suitably electrically connected to an analog to digital converter 162 which converts analog signals to digital signals. The strain gauges 114, 115 are suitably electrically connected to the analog to digital converter 162. In the embodiment shown, the strain gauges 114, 115 are illustrated as being interconnected to an amplifier 163 for amplification of the output signals from the strain gauges 114, 115. In addition, the amplified signals output from the amplifier 163 are passed through a low pass filter 165 for filtering out background noise and other unwanted signal interference. The signal frequency output from the low pass filter 165 is roughly four hundred (400) hertz (Hz). The output from the low pass filter function 165 is transferred to sample/hold circuitry 167 which periodically samples the output from the low pass filter 165 and then outputs the sensed electrical signal value to the analog to digital converter 162. The electrical connection between the strain gauges 114, 115 in the housing 105 and the amplifier 163 in the control unit are represented by the reference numeral 160 while the electrical interconnection between the position sensor 131 and the analog to digital converter 162 is represented by the line 161. It will be appreciated that the amplifier 163, low pass filter 165, sample/hold 167, and analog to digital converter functions 162 might be achieved by conventional well known circuitry.

The control unit 116 is further illustrated in FIG. 9 as including a microprocessor 164. It will be appreciated that numerous microprocessors might be utilized in keeping with the present invention; e.g. Intel 8088 and 8086. Motorola 6800, etc. The microprocessor 164 is shown as including a power supply 166 and a nickel cadmium battery 169. In addition to providing power to the control unit 116 in its operational state, and to a lesser degree, in its idle state, the power supply 166 also provides power to the position sensor 131 and the strain gauge or gauges 114, 115. The microprocessor is also illustrated as including nonvolatile data memory 168 for storing data and nonvolatile program memory 170 for storing a control program. The memory 168 might be low power CMOS memory which can be read and written into and is powered by the battery 169. The memory 170 might be electrically programmable read only memory (EPROM). The control unit 116 is further illustrated as including a real time clock 172 including an alarm function. In alternate embodiments, a speaker and a voice synthesizer might be used to provide voice commands and information to the user. In addition, the control unit 116 is illustrated as including a keypad 174 for user input into the control unit. It will be appreciated that any number of user input devices might be utilized: e.g., a keypad having individual keys, a touch sensitive pad, etc. The control unit 116 is further illustrated as including a graphic liquid crystal display 176 for displaying graphics and text information and suitable user alerts. The display 176 can have various resolutions e.g., a 240 by 120 pixel display might be used. Once again, it will be appreciated that numerous display apparatus might be utilized in keeping with the present inventions. Additionally, the control unit 116 is illustrated as including a piezo alarm 178 for providing audible alerts to the user.

The control unit 116 is further illustrated as including an ETA 232 C asynchronous communications port 180 on the microprocessor 164 for enabling communications with the devices remote from the control unit 116. It will be appreciated that more than one communications port might be present and/or that multiple communication protocols might be utilized. There are several uses to which the communications port capability can be applied. For example, information can be down loaded from the microprocessor memory 168 to a printer/plotter for printout of selected information. In addition, data might be down loaded from the memory 168 of the microprocessor 164 to an external storage device having removable media so as to enable transfer of the data to a remote location. Yet in other embodiments, a communications port might provide for wireless transmissions from the microprocessor 164 to a remote host such as a microcomputer in the doctor's office or clinic. The communications port 180 might provide for interconnection to a modem such that the user patients can down load data into their doctor's computer system by use of to modem from their home or office. Still another application for a communications port would be to enable direct electrical connection between the microprocessor 164 and another computer. This would allow down loading of data from the memory 168 of the microprocessor 164 by interconnecting the microprocessor 164 to a suitable computer. For example, the user patient might come into the clinic on a periodic basis and have a technician connect the control unit 116 to a suitable computer in the clinic on a periodic basis and have a technician connect the control unit 116 to a suitable computer in the clinic and down load the data for analysis by the doctor while the user patient was at the clinic or at some later time.

Figure 10:
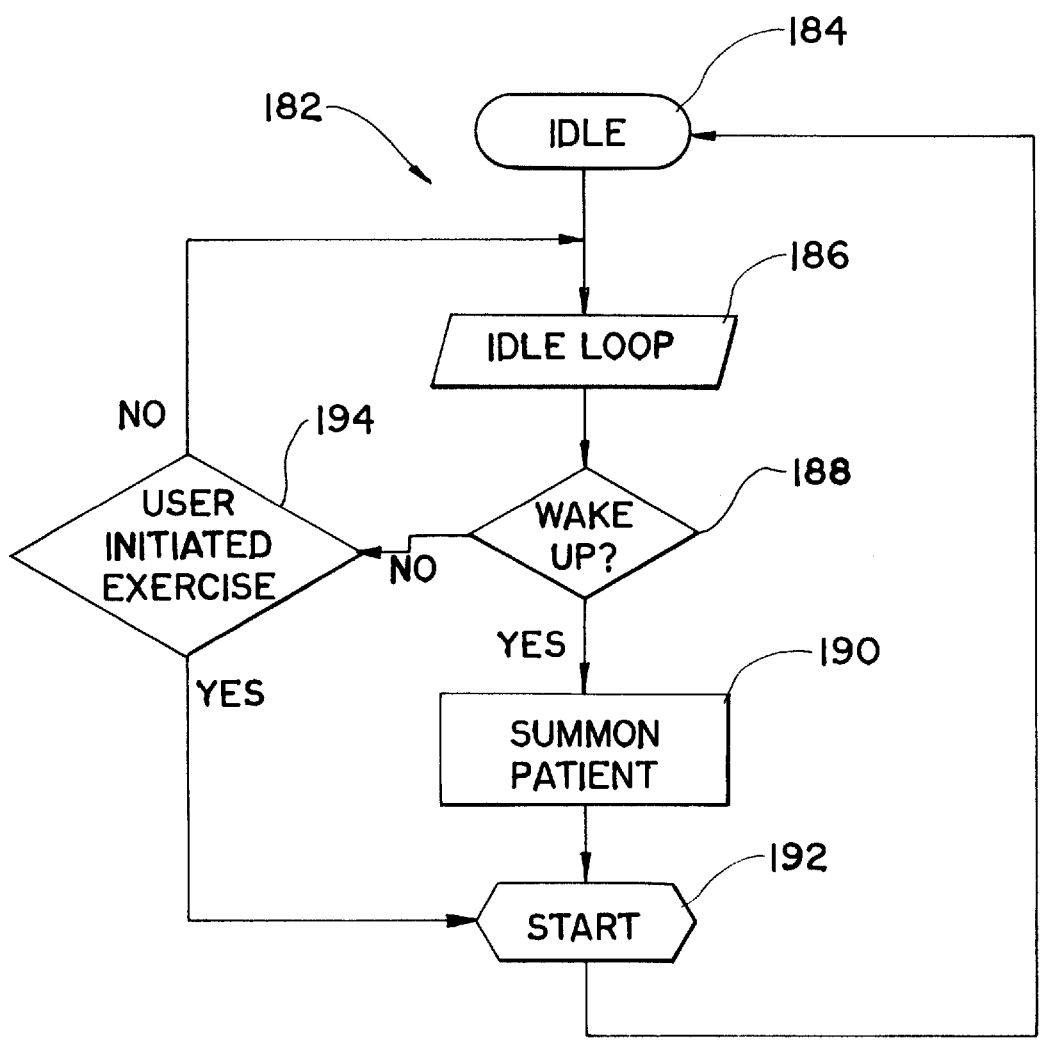
FIGS. 10, 11, and 12 are functional flow diagrams of control logic for an orthopedic device in accordance with the principles of the present invention.
Figure 11:
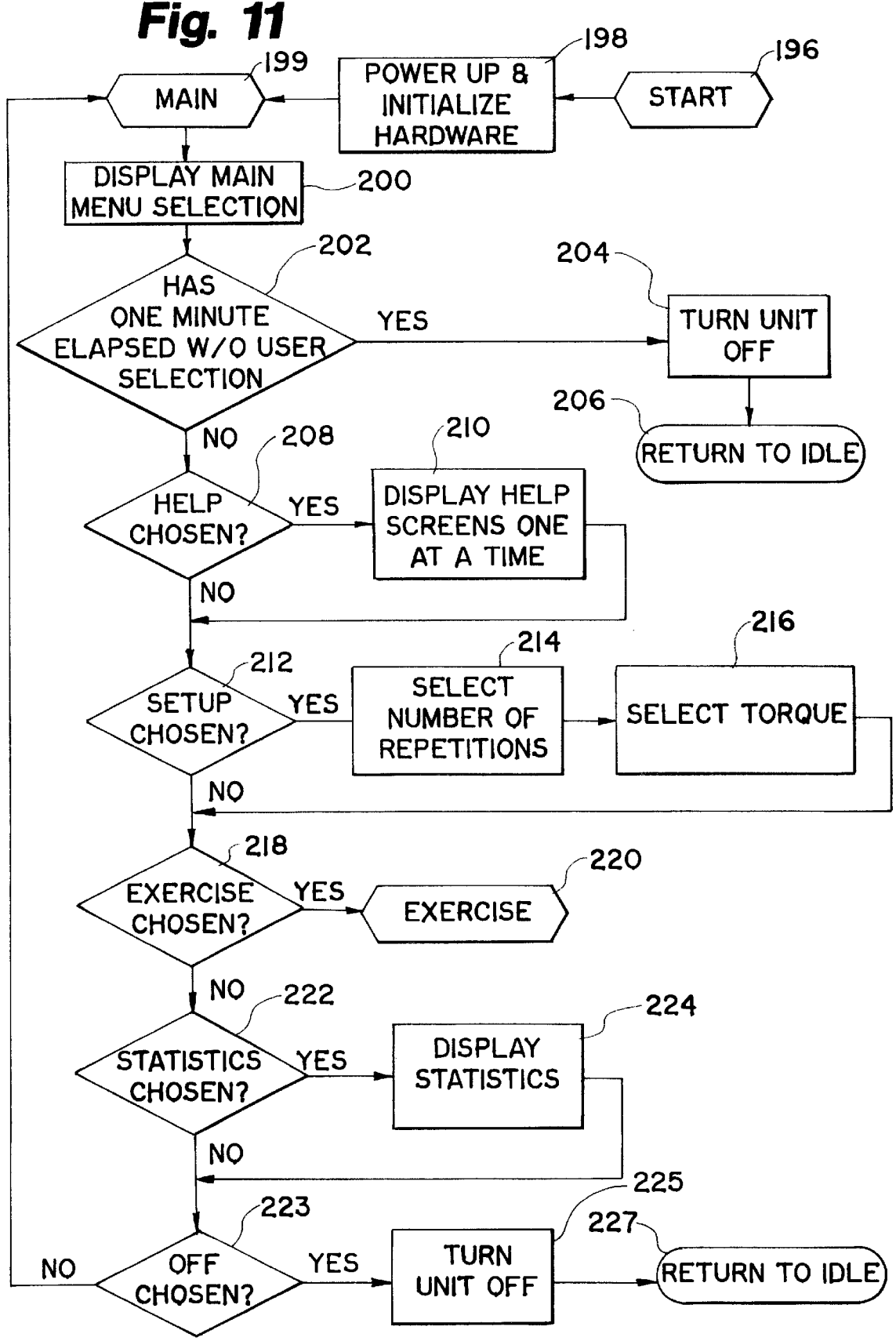
Figure 12:
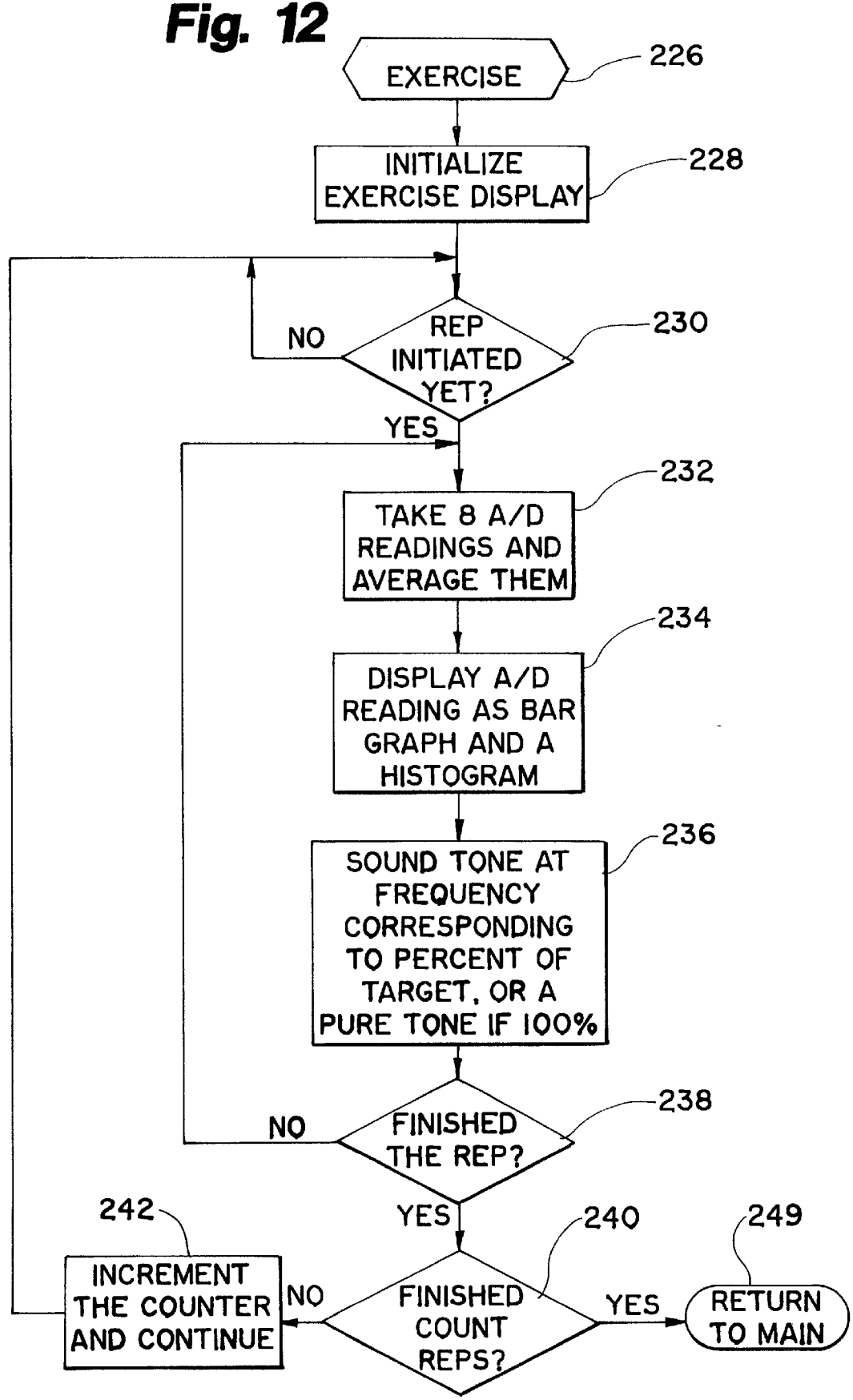

Referring now to FIGS. 10, 11, and 12 there is illustrated a functional flow diagram of control logic for an orthopedic device in accordance with the principals of the present invention. It will be appreciated that numerous embodiments of the control logic might be implemented and yet be in keeping with the principals of the present invention. Moreover, various levels of capabilities and features can be incorporated into the control logic so as to provide the orthopedic restraining device 100 with a wide range of features and applications. In the embodiment shown, the control logic is embodied in control program 182 stored in the memory 170 of the microprocessor 164. In the embodiment shown, thirty-two kilobytes (32 kB) of memory storage is used for both data and the control program 182.

During typical operation, the control unit 116 will be in an idle state requiring minimal power. During this idle state, the control program 182 will periodically check the real time clock 172 to see if the elapsed time is such that it is time for the user patient to exercise. This is best illustrated in FIG. 10 wherein the control program will go into an idle loop for a predetermined period of time. A check is then made at block 188 to see if the elapsed time is such that it is time for the user patient to exercise. If this is the case, then at block 190 the control program 182 will summon the patient by use of an audible, palpable and/or a visual alarm. The audible alarm might be executed by use of the piezo alarm 178 as illustrated in FIG. 9. The visual alarm might take the form of a flashing indicator or the like on the display 176. A palpable alarm could take the form of a common electromechanical vibrator 177. After summoning the patient at block 190, the control program 182 at block 192 then calls on a start subroutine illustrated in FIG. 11. At block 188, if it is not yet time to summon the patient, the control program 182 at block 194 checks to determine if the user patient has initiated an exercise. If at block 184 the user has requested initiation of an exercise then the control program 182 calls on the start subroutine at block 192. However, if the user has not initiated an exercise, then the control program 182 returns to the idle loop. It will be appreciated that in some embodiments of the present invention, both of the function represented by blocks 194 and 188 may not be present. For example, if the doctor does not want the patient to initiate his/her own exercise, the function represented by block 194 might be deleted from the control program 182. In this case, at block 188, if it is not yet time to summon the patient, the control program once again returns to the idle loop 186. In yet other embodiments, the user patient might be allowed to initiate exercise only if the torque (foot pounds of force) selected by the user patient to be applied by the user is within a predetermined limit. If this were the case, there would be an additional logic clock to see if the performed torque was within the guidelined limit. It will be appreciated that various alternative scenarios might be utilized and still be in keeping with the principles of the present invention.

The control logic for an embodiment of the start subroutine 192 is illustrated in FIG. 11. The start subroutine begins at block 196. At block 198 the control unit 116 powers up to a full operational power level and initializes the hardware including the sensors of the orthopedic restraining device 100. At block 199, the control program 182 enters a subroutine named MAIN which is a menu display subroutine for displaying various menus on the display 176. At block 200 a main menu selection displaying various user patient options/modes of operation is displayed on the display 176. In the embodiment shown, the following options are displayed as the main menu: Help, Setup, Exercise and Statistics. The control program 182 then checks if the user patient has made a selection within a predetermined period of time; e.g., one minute, at block 202. If no user patient selection occurs within this predetermined time interval, the control program 182 then turns off the control unit 116, i.e., powers the control unit 116 down to its idle state, at block 204. At block 206 the control program 182 returns to the idle state and will remain there until it is time to summon the user patient for a scheduled exercise or until the user patient initiates an exercise. At block 208 a check is made if the user patient has selected the help option. If the user has selected the help option, then at block 210 the control program 182 displays the various help screens one at a time. The help screens will provide the user patient with the information necessary to operate the control unit 116. If the help option was not selected by the user at block 208, then at block 212 the control program 182 checks to see if the user patient selected the setup option. If the user patient has selected the setup option at block 212, then at block 214 the display prompts the user patient to select the number of exercise repetitions, which the user patient does at that time.

At block 216 the display prompts the user to select the force (torque) to be applied, which the user does at that time. In alternate embodiments, the force (torque) to be applied is preset by the prescribing professional. The number of repetitions and torque preferably have a default value which is preset by the doctor or prescribing professional. In some embodiments, after being preset, the user will not be able to change these default values. It will be appreciated that various parameters and restrictions might be placed on the setup functions of the control program 182. For example, the patient might be allowed to select from within predetermined parameters the number of repetitions and the force (torque) to be applied. The control program 182 might be programmed to vary the number of repetitions and force (torque) requirement throughout the user patient's recovery/exercise term. The setup options might be limited such that the patient can only select additional exercise and not less than that prescribed by the doctor. Moreover, the patient might be forced to select within a range of force (torque) values. In the preferred embodiment, the orthopedic restraining device 100 has an operational torque range of from zero to one thousand foot pounds. It will be appreciated that, in alternate embodiments, this range might vary depending upon the joint being exercised and/or the parameters specified by the healthcare professional. The keypad 174 will preferably include numeric keys, direction keys, and other predetermined function keys such as an enter key to enter the selected value. The selected number of repetitions, number of exercise times per day, time of day to exercise, etc. might be selected by using up, down, and sideways keys with the enter key being used to enter a selected value into the system.

Next the control program 182 checks to see if the exercise option is selected by the user patient at block 218. If the exercise menu is selected at block 218, then at block 220 the control program 182 calls on an exercise subroutine, an embodiment of which is illustrated in FIG. 12. If the exercise option is not chosen at block 218, then at block 222 the control program 182 checks if the statistics option is selected by the user patient. If the statistics option is chosen by the user patient, then at block 224 various statistical information is displayed on the display 176 with sensed stress data obtained from a prior exercise. If the statistics option was not chosen at block 222, then at block 223, the control program 182 checks to see if the user patient has selected the off option so as to exit the menu display subroutine. If so, at block 225, the control program 182 powers the control unit 216 down to its idle state. At block 227, the control program 182 returns to the idle state. If off was not chosen at 223, the control program 182 will then return to displaying the main menu at block 199. It will be appreciated that numerous types of statistical displays might be provided to the user on the display 176. For example, a curve might be displayed wherein the area under the curve represents the work or effort performed (total energy exerted) by the patient during a particular exercise cycle. Yet another type of statistical display might be a display of the variance between the exercise goal and the actual exercise accomplished. Moreover, much more elaborate statistical analysis might be provided at a host computer such that upon down loading the data from the control unit 116, the host computer can provide a number of different statistical analyses.

An embodiment of the exercise subroutine is illustrated in FIG. 12 the exercise subroutine begins at block 226. At block 228, the control program 182 initializes the exercise display presentation which is displayed on the liquid crystal display 176. At block 230, the control program 182 checks if the user patient has begun an exercise repetition. This is determined by sensing a force (torque) being exerted by the user patient in the proper direction. Once the user patient has started a repetition at block 232 the control program 182 will take a predetermined quantity of signal readings as received from the analog digital converter 162 and average them. At block 234, the control program 182 will display the readings from the strain gauges as the strain sensed by the strain gauges 114, 115. In one embodiment, the signal readings are averaged. The averaged signals are then displayed as a bar graph or a histogram on the display 176. At block 236, the control program 182 sounds a tone at a frequency corresponding to a percent of the targeted exercise force (torque) be exerted by the user patient and will sound a continuous tone if the user patient achieves the targeted exercise force. At block 238 the control program 182 will check to see if the user patient has finished a particular repetition. If not the control program 182 will continue to take readings and averaging them. If the repetition is finished, then at block 240, the control program 182 will check if the user patient has completed the number of repetitions designated by the doctor and/or selected by the user patient. If the user patient has not finished his/her repetitions, then at block 242 the repetition counter is incremented and the control program 182 continues taking readings. Between repetitions, the control program 182 calculates the work or energy exerted by the user patient and might display the energy exerted as a percentage of the targeted energy amount. Stress data obtained during the exercise is saved or recorded for subsequent statistical analysis, displaying, recording and/or downloading to another computer. If the user patient has finished the designated number of repetitions, then at block 249 the exercise program 182 returns to the start program in FIG. 11 at the location where it initiated the exercise program such that the start program continues its normal execution and will check at block 222 to see if the statistics option was chosen.

From the above discussion it will be appreciated, that the control unit 116 might have various levels of functions. In the most basic configuration the control unit 116 might simply indicate sensed stress, display data and/or store data. Additionally, although in the preferred embodiment of the control unit 116 mounted on the housing 105 includes all the features shown in FIG. 9, it will be appreciated that some of these features might not be present and/or that other features might be contained in a separate ambulatory housing which is interconnected to the control unit 116 when desired. For example, the keyboard and display features might be present in a separate hand held housing. Alternatively, the entire control unit 116 can be wired or wirelessly interconnected for receiving outputs from the strain gauge or gauges 114, 115, and/or other elements of respective embodiments of the present restraining device, only when desired by the user.

Figure 13:
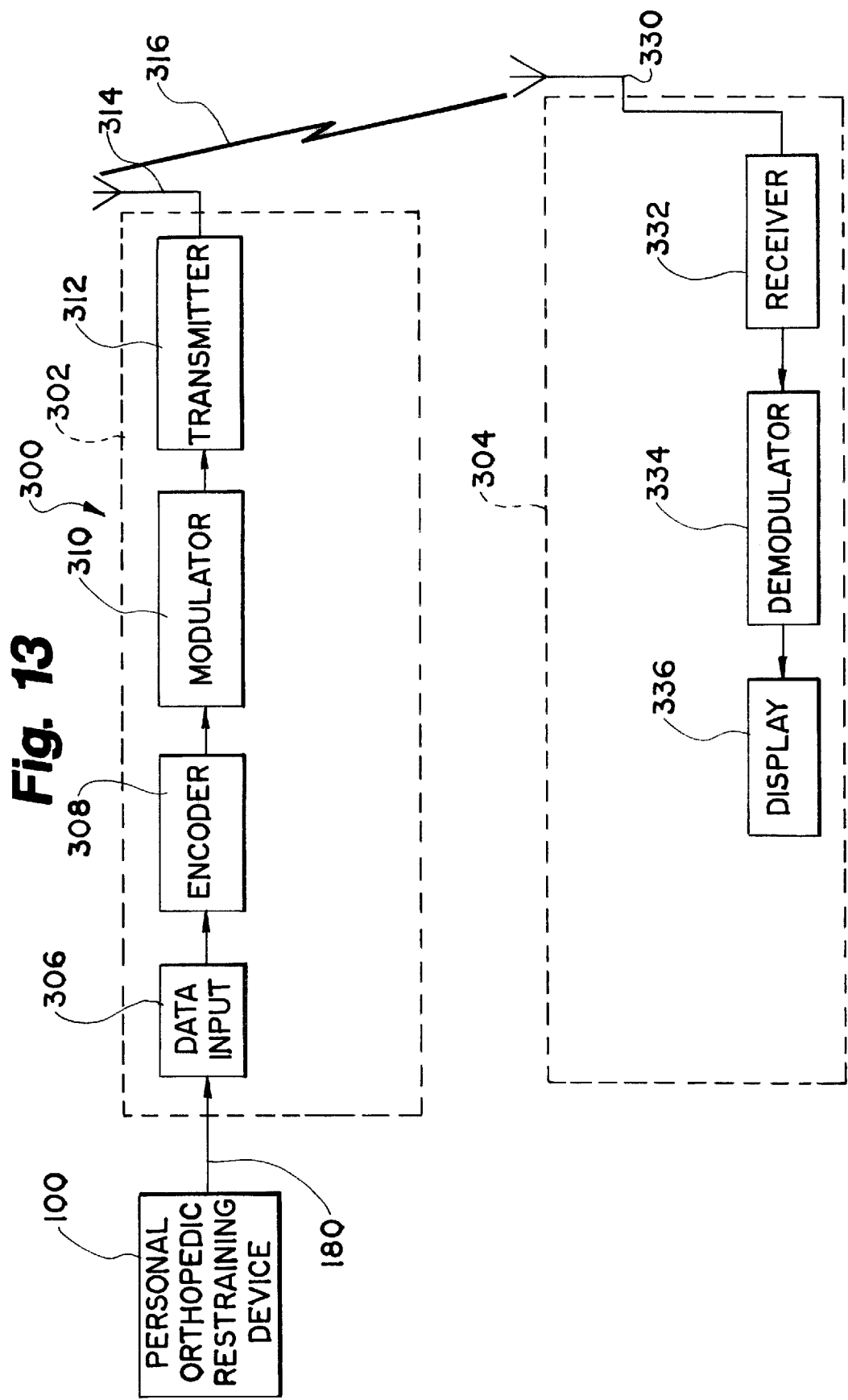
FIG. 13 is a block diagram showing a preferred embodiment local monitoring system in accordance with the present invention.
Figure 14:
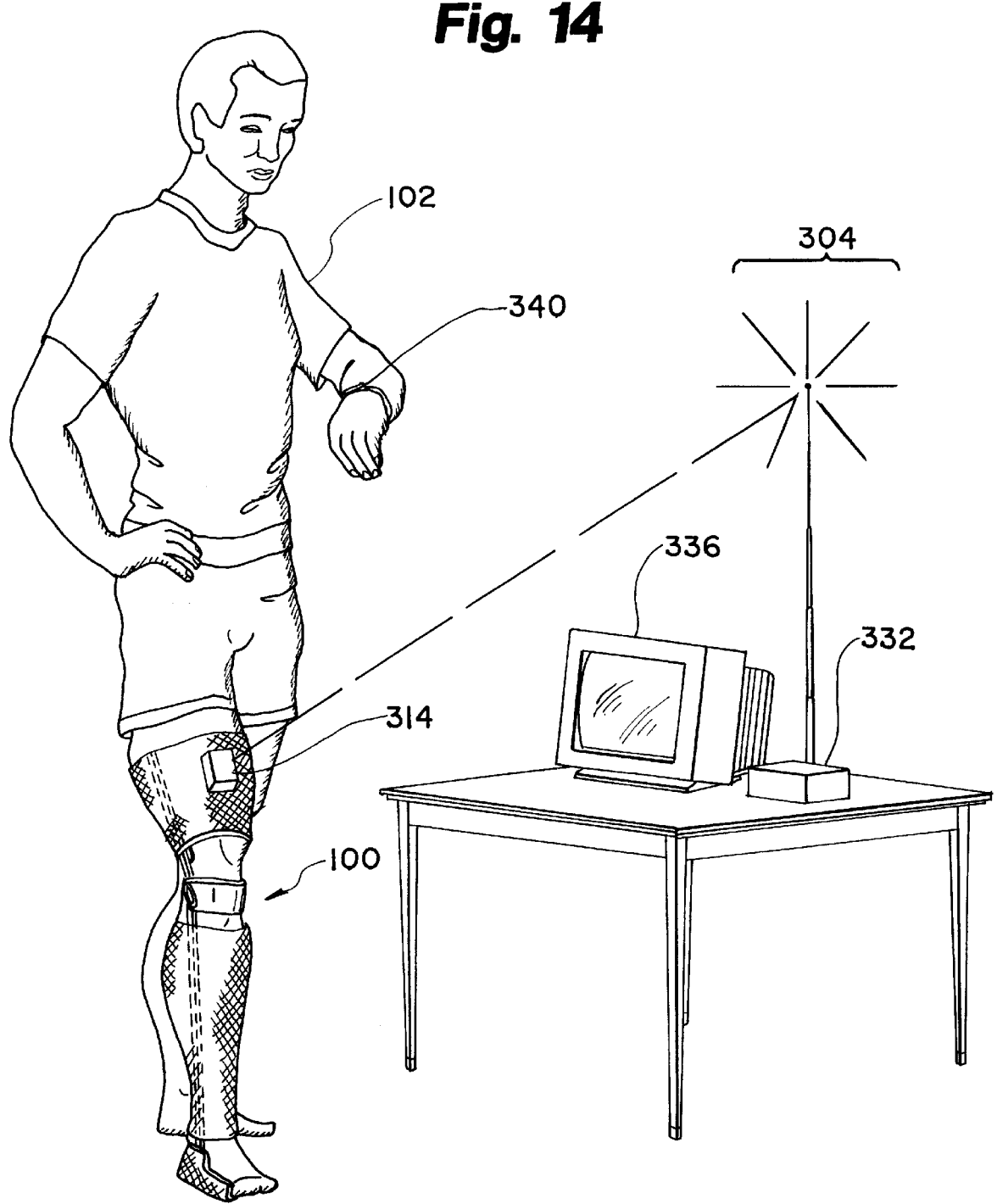
FIG. 14 is a block diagram showing the preferred embodiment local monitoring system shown in FIG. 13 at a high level view.

Referring now to FIG. 13, a block diagram of a preferred embodiment local monitoring system 300 in accordance with the present invention for use with an instrumented orthopedic restraining device 100 (e.g., a brace) is shown. This local monitoring system 300 incorporates the functions of the display 176 and the output port 180 previously described above and extends the functionality to include a display mechanism 336 which is not mounted on the personal orthopedic restraining device 100. The following discussion will focus on a simplified radio communication channel operating between the personal orthopedic restraining device 100 coupled to a communication unit 302 and a local monitoring station 304. FIG. 14 displays a general arrangement with a patient 102 wearing orthopedic restraining device 100 at a less bent angle in the vicinity of local monitoring station 304. However, it will be appreciated by those skilled in the art that a more complex communication channel may be readily used without departing from the scope and spirit of the present invention.

The communication unit 302 includes a data input 306 which receives a message signal from a controller 164 via restraining device output port 180 on personal orthopedic restraining device 100. The restraining device 100, previously described in reference to FIGS. 1–12 is designed to restrain movement of a first flexibly connected body portion relative to a second flexibly connected body portion of an individual who is wearing the restraining device. However, a more detailed discussion of the reasons behind using the orthopedic restraining device 100 and the therapeutic techniques for using the device 100 are more thoroughly discussed in the previously identified related U.S. Pat. No. 5,052,375 which is entitled "Instrumented Orthopedic Restraining Device And Method Of Use".

Also, it should be noted that previously identified related U.S. patent application Ser. No. 08/xxx,xxx which is entitled "Communication System For An Instrumented Orthopedic Restraining Device And Method Therefor" describes a more robust communication system which is capable of transmitting signals over long distances on various types of communication channels such as a satellite link or a cellular radio communication channel such that monitoring of several orthopedic restraining devices can be accomplished at a central site.

The asynchronous serial port 180 described above can take many other forms including a parallel port, Personal Computer Memory Card International Association (PCMCIA) interface, or RJ-11 phone jack; however, for the purposes of the following discussion an RS-232 serial port 180 is assumed to be used as the data output 180 line of the restraining device 100.

The message signal received by the data input 306 preferably includes one or more of the following: a message to the individual wearing the personal orthopedic restraining device from a central site monitoring station (e.g., a doctor's instructions), a message to initiate an exercise regimen, and/or a representation of a variance between an exercise goal and a current exercise regimen. In addition, the message signal preferably consists of display driver commands which can be directly used by a display device to drive a display mechanism 336. By way of example, it will be assumed that the message signal contains 100 data bits of information. It will be appreciated by those skilled in the art that this choice of 100 data bits is only to facilitate the following discussion. The message signal can readily contain more or less data bits while not departing from the scope and spirit of the present invention.

An encoder 308 is operatively coupled to the data input 306 to encode the message signal into a display compatible signal. It will be appreciated by those skilled in the art that several display compatible signals exist including enhanced graphics adapter (EGA) commands, video graphic array (VGA) commands, liquid crystal display (LCD) actuating commands, and light emitting diode (LED) array diode illuminating commands. The optimal encoding techniques for a particular monitoring system vary depending upon the particular display device used. For the preferred embodiment of the present invention, an LCD is used as display 336 and the display compatible signal preferably consists of LCD segment illuminating commands. In continuing the example, the 100 data bits of the message signal can be encoded such that roughly 200 are generated. It will be appreciated that the number of LCD segment illuminating commands will vary, depending upon the particular alphanumeric or graphic characters which are to be displayed (e.g., to display the letter "I", it may take two segment illuminating commands whereas to display the letter "O" it may take eight segment illuminating commands).

A modulator 310 is operatively coupled to the encoder 308 to prepare the display compatible signal for subsequent transmission by modulating the display compatible signal. Several forms of modulation exist. The display signal can be modulated according to a communication access type selected from the group consisting of: amplitude modulation (AM) and frequency modulation (FM). For the preferred embodiment, FM modulation is used. In continuing the example, the 200 segment illuminating commands (i.e., display compatible signal) are used to frequency modulate an FM carrier signal. It will be appreciated by those skilled in the art that FM modulators are well known in the art and as such do not need to be described further herein.

Further, a transmitter 312 is operatively coupled to the modulator 310 to transmit the modulated display compatible signal over a communication channel 316 by radiating a radio signal on antenna 314 such that such that the individual wearing the restraining device 100 can receive messages from the restraining device controller 164. The communication channel 316 may be one of several types of media (i.e., channels) including: an electronic data bus, radio communication link, wireline, and/or optical fiber link. The type of communication channel 316 can also be described which reference to a particular channel known in the art. Some of the possible currently existing channels that may be used include a serial port wireline, a parallel port wireline, an infra-red link, and/or a radio link. For the preferred embodiment, as a radio communication link is used as the communication channel 316. In the example, the FM carrier signal preferably is centered on a frequency from the 45 to 50 MegaHertz frequency band. This frequency band has been reserved by the FCC and other similar agencies around the world for use by unregulated personal communication devices such as patio phones and baby monitors. By using this same frequency band for the local monitoring system communications, several FCC licensing and/or regulations can be avoided. It will be appreciated by those skilled in the art that the principles described herein can readily be applied to communication channels operating at different frequencies and over different media without departing from the scope and spirit of the present invention.

Referring back to the example, the 200 segment illuminating commands are used to FM modulate a frequency oscillator to form an output signal. The output signal is bandpass filtered, translated to a radio frequency (RF), amplified, filtered, and radiated by the antenna 314 to complete transmission of the display compatible signal in the communication channel 316 with FM modulation.

A local monitoring unit 304 also is provided in the preferred embodiment communication system 300. The local monitoring unit 304 operates in a manner similar to the that which was described above for the communication unit 302; however, in reverse order. The local monitoring unit 304 includes a receiver 332 for receiving a modulated display compatible signal from a personal orthopedic restraining device 100 worn by an individual 102 via antenna 330. A demodulator 334 is operatively coupled to the receiver 332 to demodulate the received modulated display compatible signal into a display compatible signal. A video display 336 is operatively coupled to the demodulator 334 to display a message from the restraining device controller based on contents of the display compatible signal. The local monitoring unit 304 can be placed in a wrist watch 340 (see FIG. 14) to allow convenient reference by the patient 102.

As previously noted with respect to the communication unit 302 attached to the restraining device 100, the local monitoring unit 304 preferably is adapted for use with a variety of different types of communication channels and different modulation schemes. In addition, the message from the restraining device controller preferably consists of a message to the individual 102 wearing the personal orthopedic restraining device 100 from a central site monitoring station, a message to initiate an exercise regimen, and/or a representation of a variance between an exercise goal and a current exercise regimen. This latter message can perform the same function that the piezo alarm 178 does in the above description for letting that individual 102 know that the exercise regimen is being performed according to the pre-defined specifications. In particular a sine waveform or square waveform, representing the torque load characteristics of the prescribed exercise regime can be displayed along side the actual torque output by the individual 102 as measured by the strain gauges 114,115 and output as a waveform. When the individual 102 is performing the exercise regimen exactly as prescribed, the two waveforms, as displayed, will be identical.

The video display 336 preferably includes a video source input (not shown) operatively coupled to the demodulator 334 such that the display compatible signal directly drives a display mechanism within the video display 336. This display mechanism may be one of several kinds, including: a liquid crystal display, a light emitting diode array, and/or a cathode ray tube video monitor.

The present invention also can be described in reference to a device-implemented method steps 400–416 shown in FIG. 15 which detail preferred embodiment operations of the local monitoring system 300 as shown in FIG. 13. This device-implemented method is used to communicate an message signal between a personal orthopedic restraining device 100 and a local monitoring unit 304. The local monitoring/communication method includes receiving 402 a message signal from a restraining device controller 164 operatively coupled to the personal orthopedic restraining device 100. Subsequently, the message signal is encoded 404 into a display compatible signal. The display compatible signal is prepared 406 for subsequent transmission by modulating the display compatible signal. Finally, the modulated display compatible signal is transmitted 408 over a communication channel 316 to the local monitoring unit 304 such that the individual 102 wearing the restraining device 100 can receive messages from the restraining device controller 164.

The method also includes receiving 410 a modulated display compatible signal over a communication channel 316 from a personal orthopedic restraining device controller 164 at the local monitoring unit 304. Subsequently, the received modulated display compatible signal is demodulated 412 into a display compatible signal. Finally, a message from the restraining device controller 164 based on contents of the display compatible signal is displayed 414.

This message signal from the personal orthopedic restraining device controller 164 preferably is either a message to the individual 102 wearing the personal orthopedic restraining device 100 from a central site monitoring station, a message to initiate an exercise regimen, or a representation of a variance between an exercise goal and a current exercise regimen.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of shape, size and arrangement of parts within the principles of the present invention to the full extent indicated by the broad general meaning of the terms in which the appended claims are expressed.

What is claimed is:

1. A communication unit, comprising:
   (a) data input means for receiving a message signal from a restraining device controller operatively coupled to a personal orthopedic restraining device, the restraining device restraining movement of a first flexibly connected body portion relative to a second flexibly connected body portion of an individual wearing the restraining device;
   (b) encoder means, operatively coupled to the data input means, for encoding the message signal into a display compatible signal;
   (c) modulator means, operatively coupled to the encoder means, for preparing the display compatible signal for subsequent transmission by modulating the display compatible signal; and
   (d) transmitter means, operatively coupled to the modulator means, for transmitting the modulated display compatible signal over a communication channel to a local display device such that the individual wearing the restraining device can receive messages from the restraining device controller.

2. The communication unit of claim 1 wherein the message signal is selected from the group consisting of: a message to the individual wearing the personal orthopedic restraining device from a central site monitoring station, a message to initiate an exercise regimen, and a representation of a variance between an exercise goal and a current exercise regimen.

3. The communication unit of claim 1 wherein the message signal comprises display driver commands which can be directly used by a display device to drive a display mechanism.

4. The communication unit of claim 1 wherein the modulator means comprises means for modulating the display compatible signal according to a communication access type selected from the group consisting of: amplitude modulation and frequency modulation.

5. The communication unit of claim 1 wherein the communication channel is selected from the group consisting of an electronic data bus, radio communication link, wireline, and optical fiber link.

6. The communication unit of claim 1 wherein the transmitter means comprises means for transmitting the modulated display compatible signal over a communication channel of a type selected from the group consisting of a serial port wireline, a parallel port wireline, an infra-red link, and a radio link.

7. A local monitoring unit, comprising:
(a) receiver means for receiving a modulated display compatible signal over a communication channel from a personal orthopedic restraining device controller;
(b) demodulator means, operatively coupled to the receiver means, for demodulating the received modulated display compatible signal into a display compatible signal; and
(c) video display means, operatively coupled to the demodulator means, for displaying a message from the restraining device controller based on contents of the display compatible signal.

8. The local monitoring unit of claim 7 wherein the communication channel is selected from the group consisting of an electronic data bus, radio communication link, wireline, and optical fiber link.

9. The local monitoring unit of claim 7 wherein the receiver means comprises means for receiving the modulated display compatible signal over a communication channel of a type selected from the group consisting of a serial port wireline, a parallel port wireline, an infra-red link, and a radio link.

10. The local monitoring unit of claim 7 wherein the message from the restraining device controller is selected from the group consisting of: a message to the individual wearing the personal orthopedic restraining device from a central site monitoring station, a message to initiate an exercise regimen, and a representation of a variance between an exercise goal and a current exercise regimen.

11. The local monitoring unit of claim 7 wherein the video display means includes a video source input operatively coupled to the demodulator means such that the display compatible signal directly drives a display mechanism within the video display means.

12. The local monitoring unit of claim 11 wherein the display mechanism is selected from the group consisting of: a liquid crystal display, a light emitting diode array, and a cathode ray tube video monitor.

13. A local monitoring system for a personal orthopedic restraining device where the restraining device restrains movement of a first flexibly connected body portion relative to a second flexibly connected body portion of an individual wearing the restraining device, the local monitoring system comprising:
(a) data input means for receiving a message signal from a restraining device controller operatively coupled to the personal orthopedic restraining device;
(b) encoder means, operatively coupled to the data input means, for encoding the message signal into a display compatible signal;
(c) modulator means, operatively coupled to the encoder means, for preparing the display compatible signal for subsequent transmission by modulating the display compatible signal;
(d) transmitter means, operatively coupled to the modulator means, for transmitting the modulated display compatible signal over a communication channel;
(e) receiver means for receiving the modulated display compatible signal over a communication channel from a personal orthopedic restraining device controller;
(f) demodulator means, operatively coupled to the receiver means, for demodulating the received modulated display compatible signal into a display compatible signal; and
(g) video display means, operatively coupled to the demodulator means, for displaying the message signal from the restraining device controller based on contents of the display compatible signal.

14. The local monitoring system of claim 13 wherein the message signal is selected from the group consisting of: a message to the individual wearing the personal orthopedic restraining device from a central site monitoring station, a message to initiate an exercise regimen, and a representation of a variance between an exercise goal and a current exercise regimen.

15. The local monitoring system of claim 13 wherein the modulator means and the demodulator means manipulate the display compatible signal according to a communication access type selected from the group consisting of: amplitude modulation and frequency modulation.

16. The local monitoring system of claim 13 wherein the communication channel is selected from the group consisting of an electronic data bus, radio communication link, wireline, and optical fiber link.

17. The local monitoring system of claim 13 wherein the transmitter means and receiver means each comprise means for manipulating the modulated display compatible signal over a communication channel of a type selected from the group consisting of a serial port wireline, a parallel port wireline, an infra-red link, and a radio link.

18. The local monitoring system of claim 13 wherein the video display means includes a video source input operatively coupled to the demodulating means such that the display compatible signal directly drives a display mechanism within the video display means.

19. The local monitoring system of claim 18 wherein the display mechanism is selected from the group consisting of: a liquid crystal display, a light emitting diode array, and a cathode ray tube video monitor.

20. A method of communicating an message signal between a personal orthopedic restraining device and a local monitoring unit, the restraining device restraining movement of a first flexibly connected body portion relative to a second flexibly connected body portion of an individual wearing the restraining device, the communicating method comprising the steps of:
(a) receiving a message signal from a restraining device controller operatively coupled to the personal orthopedic restraining device;
(b) encoding the message signal into a display compatible signal;
(c) preparing the display compatible signal for subsequent transmission by modulating the display compatible signal; and
(d) transmitting the modulated display compatible signal over a communication channel to the local monitoring unit such that the individual wearing the restraining device can receive messages from the restraining device controller.

21. The method of claim 20 wherein the message signal is selected from the group consisting of: a message to the individual wearing the personal orthopedic restraining device from a central site monitoring station, a message to initiate an exercise regimen, and a representation of a variance between an exercise goal and a current exercise regimen.

22. A method of communicating an message signal between a personal orthopedic restraining device and a local monitoring unit, the restraining device restraining movement of a first flexibly connected body portion relative to a second flexibly connected body portion of an individual wearing the restraining device, the communicating method comprising the steps of:

(a) receiving a modulated display compatible signal over a communication channel from a personal orthopedic restraining device controller;

(b) demodulating the received modulated display compatible signal into a display compatible signal; and (c) displaying a message from the restraining device controller based on contents of the display compatible signal.

23. The method of claim 22 wherein the message from the restraining device controller is selected from the group consisting of: a message to the individual wearing the personal orthopedic restraining device from a central site monitoring station, a message to initiate an exercise regimen, and a representation of a variance between an exercise goal and a current exercise regimen.

* * * * *